United States Patent [19]

Samuels

[11] Patent Number: 4,953,560
[45] Date of Patent: Sep. 4, 1990

[54] APPARATUS, METHOD, AND TEST KIT FOR DIAGNOSIS OF VAGINAL YEAST INFECTIONS

[76] Inventor: Bernard Samuels, 5624 Evelyn Ct., New Orleans, La. 70124

[21] Appl. No.: 447,466

[22] Filed: Dec. 7, 1989

[51] Int. Cl.⁵ .............................................. A61B 10/00
[52] U.S. Cl. ...................................... 128/759; 604/1; 435/295
[58] Field of Search ................... 128/749, 756, 759; 604/1; 435/292, 293, 294, 295

[56] References Cited

U.S. PATENT DOCUMENTS

| | | | |
|---|---|---|---|
| 3,368,549 | 2/1968 | Barr | 604/1 |
| 3,443,562 | 5/1969 | Gustafson | 604/1 |
| 4,877,037 | 10/1989 | Ko et al. | 128/756 |

Primary Examiner—Randall L. Green
Assistant Examiner—Randy Shay
Attorney, Agent, or Firm—Sughrue, Mion, Zinn, MacPeak & Seas

[57] ABSTRACT

A home diagnosis device for vaginal yeast infections comprising a support stick; a swab having loosely woven fibers attached to one end of the support stick; a growth media for culturing and diagnosing vaginal yeast infection infiltrated between the loosely woven fibers of the swab. A home diagnosis device for vaginal yeast infections comprising: an outer tube; a cap, detachably connected to one end of the outer tube; a swab element having loosely woven fibers; a growth media for culturing and diagnosing vaginal yeast infection infiltrated between the loosely woven fibers of the swab element; and a holder for the swab element slideably mounted inside the outer tube. A method for the home diagnosis of vaginal yeast infections comprising the steps of: inserting a tube into the vagina containing a swab element of loosely woven fibers between which is infiltrated a growth media for culturing and diagnosing vaginal yeast infection; sliding the swab element out of the tube and into contact with vaginal secretion; retracting the swab element into the tube and out of contact with the vaginal secretion; capping the tube; culturing the vaginal secretion in the tube containing the swab element; and examining the swab for indications of vaginal yeast infection.

20 Claims, 3 Drawing Sheets

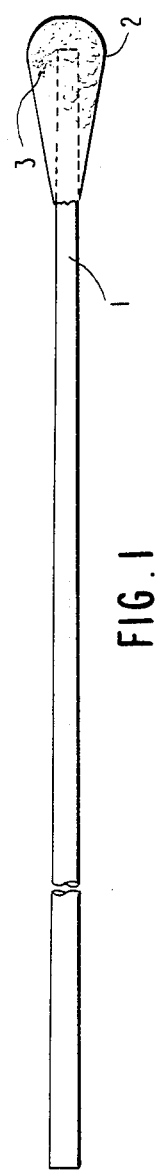
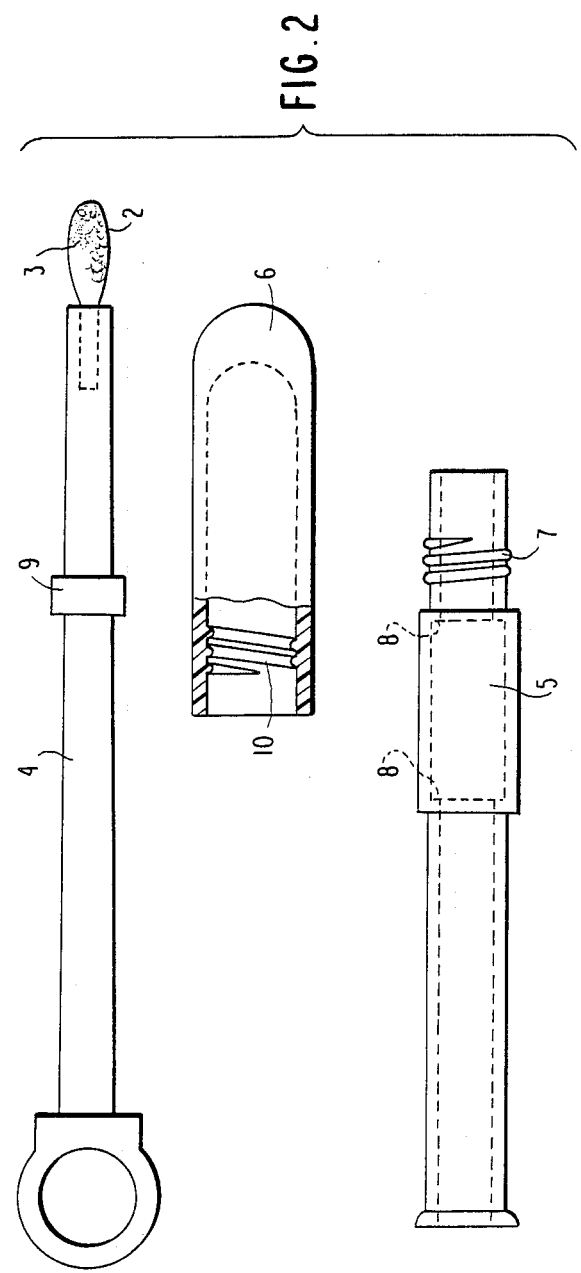

APPARATUS, METHOD, AND TEST KIT FOR DIAGNOSIS OF VAGINAL YEAST INFECTIONS

FIELD OF THE INVENTION

The present invention relates to a diagnostic test for vaginal yeast infections. In particular, the present invention relates to a diagnostic test using a novel swab element of loosely packed fibers between which is infiltrated a media for culturing vaginal yeast that produces unexpectedly large and easily discernible colonies that simplify self diagnosis of a vaginal yeast infection. More particularly, the invention relates to a swab element that is large enough for a woman to easily and safely insert into and remove from her own vagina. If vaginal yeast is present it is picked up by the swab element and penetrates below the surface of the media and between the loosely packed fibers where it begins to grow. Yeast growth between the fibers proceeds rapidly and results in large colonies that produce a visible discoloration of the surface of the swab element.

BACKGROUND OF THE INVENTION

Many types of vaginal discharge are normal and not indicative of any infection. When a woman detects what she suspects is an abnormal discharge she may wait to see if it goes away or she may try to treat herself using readily available over-the-counter remedies before visiting her physician for treatment. Delaying treatment or self treatment often results in an exacerbation of the infection.

Similarly, vaginal itching, while not normal, is not necessarily indicative of any infection. When a woman detects vaginal itching, however, she suspects an infection and usually seeks medical attention immediately. Frequently, the itching is due to an allergy or physical irritation rather than an infection. Because bath soap is the most common cause of such irritation many times no specific treatment is necessary. If the cause of the itching is not an infection, the condition is likely to be resolved spontaneously or through minor self treatment.

It is well known among physicians to confirm the presence of an infectious organism through the use of a variety of culture techniques. One well known technique involves inserting a cotton swab into the vagina, picking up inoculum in vaginal secretion on the swab and transferring the inoculum to a tube or petri plate containing culture medium. The plate or tube is then incubated and examined for the black or brown spots that are characteristic of yeast colonies and indicative of a yeast infection. This technique has a number of drawbacks:

(1) Much of the vaginal secretion that contacts the cotton swab is absorbed by the bottom fibers and the inoculum is not transferred to the culture medium. This decreases the sensitivity of the test. In fact so little yeast may be transferred that the characteristic colonies develop slowly, if at all, and are difficult even for trained personnel to identify.

(2) Some training is necessary to properly insert the swab into the vagina and properly transfer the inoculum to the surface of the culture medium. While not complicated, this procedure is not suitable for home use.

(3) The culture media is grayish, as are developing yeast colonies. The growing colonies are thus gray on gray, which makes it difficult for someone without experience reading cultures to pick out developing colonies on the surface of the media.

It is also well known to use a metal speculum in place of the cotton swab to transfer the vaginal secretion to the culture medium. The metal speculum increases the sensitivity of the test because much of the inoculum will eventually be transferred to the culture medium. But this advantage is more than offset by the increased cost and the amount of skill necessary to use it. Swabbing with a metal speculum also carries some risk of inadvertent laceration of the vaginal wall. In addition, the speculum must be sterilized professionally and cannot be self inserted.

U.S. Pat. No. 3,368,549 teaches replacing the cotton swab with a globule of molded culture medium, or molding a globule of culture medium over a cotton swab. This device is theoretically simpler than traditional techniques because the culture medium contacts the inoculum directly. This device is not usable, however, because of the following serious disadvantages: The inoculum is heavily concentrated in one area and the culture medium is extremely dense, because the colonies cannot penetrate the medium, even after prolonged growth, they appear as small, concentrated spots that are difficult to see without magnification, thus making the results difficult to evaluate. Also, the swab is too short and too sharp to be usable in the vagina where it could easily cause laceration.

U.S. Pat. No. 3,616,265 teaches a flattened, elongated support which carries culture medium. The support fits into a companion container that has brushes positioned over its open end. In use, the support is used to pick up inoculum directly and when the support is inserted in its companion container the brushes contact the medium and spread the inoculum out on the culture medium. Because the brushes must be positioned to brush the media at the correct level, this device is complex and expensive to manufacture. Additionally, the support is hard like a speculum and swabbing must be performed carefully.

U.S. Pat. Nos. 4,653,510 and 4,485,824 both teach using swab elements enclosed in companion tubes that can contain culture media. The tube, which contains either a cotton wadding swab element or one of firmly wound rayon filament, is inserted in the vagina where the swab element is extended from the tube to pick up the inoculum. Retracting the swab element back into the tube brings the inoculum into contact with the media. This device is also complex with close tolerances between its parts. The media is dense and hard and because the inoculation takes place inside the tube one must look through the medium to try to see if any yeast colonies are visible. These devices are designed primarily to prevent contamination of a swab element once it has picked up targeted inoculum and contain a series of scored break points and sealing gaskets. They are complicated to use and manufacture making them too inconvenient and expensive for home use.

None of the known culturing devices have significantly replaced the traditional smear and culture technique. This is because all the devices achieve a one step culture through increased complexity and cost. All of the described devices are too cumbersome and intimidating for non-professional use. They are too expensive for any but the affluent to purchase, and potentially dangerous. They are unsuitable for use by young people. Brushes, traditional cotton swabs, and the like easily traumatize the delicate mucous membranes of the genito-urinary system. There is no device available that could be used by the average woman for self diagnosis of vaginal yeast infections.

A simple, accurate, and inexpensive device is therefore desired to replace the traditional swab and smear technique and the current one step swab/culture devices. In addition, a device that can be easily adapted for home use for the diagnosis of vaginal yeast infection is greatly desired.

SUMMARY OF THE INVENTION

One object of the present invention is to provide a simple, uncomplicated device that the average woman can use on herself to determine if she has a vaginal yeast infection.

This and other objects of the invention have been achieved by providing a diagnosis device for vaginal yeast infections comprising: a support stick; a swab having loosely woven fibers attached to one end of said support stick; and a growth media for culturing and diagnosing vaginal yeast infection infiltrated between said loosely woven fibers of said swab.

In another embodiment the invention also provides a home diagnosis device for vaginal yeast infections comprising: an outer tube; a cap, detachably connected to one end of said outer tube; a swab element having loosely woven fibers; a growth media for culturing and diagnosing vaginal yeast infection infiltrated between said loosely woven fibers of said swab element; and a holder for said swab element slideably mounted inside said outer tube.

In still another embodiment the present invention provides a method for diagnosis of vaginal yeast infections comprising the steps of: spreading the lips of the vulva; inserting into the vagina a swab of loosely woven fibers between which is infiltrated a growth media for culturing and diagnosing vaginal yeast infection; contacting vaginal secretion; removing said swab from the vagina; placing said swab in a sterile container; covering said container; culturing said vaginal secretion; and examining said swab for indications of vaginal yeast infection.

In another embodiment the present invention provides a method for diagnosis of vaginal yeast infections comprising the steps of: inserting a tube into the vagina, said tube containing a swab element of loosely woven fibers between which is infiltrated a growth media for culturing and diagnosing vaginal yeast infection; sliding said swab element out of said tube and into contact with vaginal secretion; retracting said swab element into said tube and out of contact with said vaginal secretion; capping said tube; culturing said vaginal secretion in said tube containing said swab element; and examining said swab for indications of vaginal yeast infection.

In an even further embodiment, the present invention provides a test kit for diagnosis of vaginal yeast infections comprising: (a) a diagnosis device for vaginal yeast infections comprising a support stick, a swab having loosely woven fibers attached to one end of said support stick, and a growth media for culturing and diagnosing vaginal yeast infection infiltrated between said loosely woven fibers of said swab; and (b) a closable container receiving said support stick and swab for culturing vaginal secretion on said growth media of said device.

BRIEF DESCRIPTION OF THE DRAWINGS

FIG. 1 is one embodiment of the diagnosis device of the invention.

FIG. 2 is a second embodiment of the diagnosis device of the invention.

DETAILED DESCRIPTION OF THE INVENTION

Figure 5:
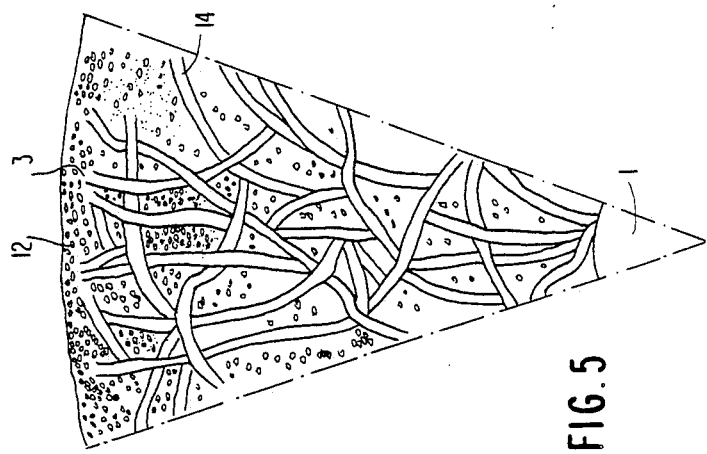
FIG. 5 is a pictorial drawing of a magnified cross-sectional view of FIG. 4 showing penetration of the yeast colonies below the surface into the media which is infiltrated between the fibers of the swab element.

The present invention provides a diagnosis device for vaginal yeast infections that comprises a swab element of loosely wrapped fibers, the swab being impregnated with a culture media for vaginal yeast such that the media is infiltrated between the fibers. Because the media is impregnated into the swab, the grayish tint of the media disappears, and the swab appears white, the color of the swab fibers. A totally unexpected property of this device is that yeast colonies develop not merely on the surface of the media, as disclosed in the prior art, but also below the surface. This unexpected use of subsurface media results in rapid and abundant growth of yeast that produces an easily discernible color change against the white surface of the swab element. The color change is so obvious, that anyone can detect it.

In the figures, like numbers refer to like elements.

With reference to the drawings, one embodiment of the home diagnosis device shown in FIG. 1 comprises a support stick 1 and a swab element 2.

The support stick can be of any suitable material such as wood, plastic or paper. Preferably the support stick is paper.

The swab element can be any loosely woven inert material and is attached to the support stick with an inert binder. By "inert" applicant means a material that is nonreactive with the human body during a period of time appropriate for the described invention. Preferably, the swab element is of white loosely woven USP (United Stated Pharmacopeia) Rayon. The swab element is preferably about 1¼ inches long and about ½ inch in diameter.

A suitable inert binder is sodium carboxymethyl cellulose.

A complete swab of loosely woven rayon, secured to a suitable support stick with sodium carboxymethyl cellulose that is appropriately sized is commercially available from the Solon Manufacturing Co, Solon, Maine under the tradename PROCTOSCOPIC APPLICATOR.

The swab element is impregnated with media 3, such that the media infiltrates between and covers the fibers. The media will withstand disintegration on insertion into the vagina and at the same time will support the growth of vaginal yeast colonies.

Table 1 gives the preferred composition of the culture media. This media is a modified BIGGY Agar manufactured by Scott Lab, Sulphur, Louisiana, for the isolation and presumptive identification of Candida species. BIGGY Agar is well known in the art as a formulation that inhibits the growth of bacteria and encourages the growth of Candida species. Of course, the skilled artisan will appreciate that modifications can be made to the preferred media without departing from the spirit and scope of this invention.

TABLE 1

An aqueous solution of:
about 3.0% Agar
about 0.5% Bismuth Ammonium Citrate
about 0.3% Sodium Sulfite
about 1.0% Dextrose
about 1.0% Glycine
(All percentages are by weight)

The swab element is impregnated with the media by submerging it into liquid media prepared by melting the premixed media in a hot water bath or by other suitable means at about 72°–78° C. and immersing the swab in the hot media until it is saturated. The swab must remain in the liquid culture media until the media has infiltrated between the fibers of the swab element. This time varies depending on the composition of the swab element. One skilled in the art can readily discern when the swab element is infiltrated with the media (i.e. when the immersed swab ceases to bubble). Using the preferred USP Rayon, the time of immersion is about 1.5–3.0 seconds. For increased storage life of the media impregnated swab it is preferred that after a short drying time, about 60 seconds, the swab be reimmersed in the hot media.

The premixed media is prepared by combining the components in water and bringing the mixture to a boil to dissolve all the components.

To use the device depicted in FIG. 1, a woman carefully spreads the lips of her vagina with one hand, using a mirror if necessary. (Essentially, the same technique as used to insert a tampon.) With the other hand holding the support stick, she inserts the swab element of the device a sufficient distance, approximately 1–2 inches, into her vagina in order to contact vaginal secretion. She then removes the device and places it in a transparent tube and caps the tube. The vaginal secretion is cultured on the swab in the tube at a temperature sufficient to produce yeast colonies if yeast is present. A suitable temperature for culturing the vaginal secretion is greater than about 50° F., preferably about 72° F. (room temperature), and most preferably at about 98.6° F. (body temperature) in order to produce the most rapid results. If the woman has a yeast infection, brown colonies begin to grow throughout the media after 12 hours and within about 16–18 hours, depending on the culturing temperature, they should cover the surface of the swab element.

The device is reliable when used at any time except immediately after douching with a medicated douche.

A second embodiment of the home diagnosis device is shown in FIG. 2. This embodiment comprises a swab element 2, an inner holder 4, an outer tube 5, and a cap 6. The outer tube 5, has threads 7 at one end and interior shoulders 8. The cap 6 has threads mating with the threads 10 on the outer tube. The swab element 2 is impregnated with media 3 and attached to the inner holder 4. The inner holder 4 has annular shoulders 9 and is slideably mounted inside the outer tube 5. When the cap 6 is removed from the outer tube 5, the inner holder 4 can be displaced relative to the axis of the outer tube 5 to extend the swab element 2 out of the outer tube. The annular shoulders 9 contact the interior shoulders 8 to assure that the swab element 2 is properly positioned when it is outside the outer tube 5 to expose the media 3 to vaginal secretion and inside the outer tube 5 before the cap 6 is placed on the tube.

In this embodiment, any suitable swab element, as described above is attached to an inner holder. The swab element is prepared as above by submerging it in liquid culture media.

The outer tube 5, cap 6, and inner holder 4, can be constructed of any material suitable for insertion into the vagina such as paper or plastic. Preferably all these parts are constructed from the same material, and the preferred material is a sterile, semi-rigid, transparent plastic.

The skilled artisan readily knows how to construct devices resembling that shown in FIG. 2.

To use the preferred embodiment of the device described above, a woman removes the cap 6 from the outer tube 5 and inserts the outer tube 5 containing the sliding inner holder 4 with the attached swab element 2 into her vagina. She pushes the swab element holder 4 to displace the swab element holder axially relative to the outer tube 5 until the annular shoulder 9 has contacted the interior shoulder 8 thus extending the media 3 impregnated on the swab element 2 outside the outer tube 5 and into contact with any vaginal secretion inside the vagina that might contain yeast. When the swab element 2 is coated with vaginal secretion, the woman pulls on the swab element holder 4 until the annular shoulder 9 and the interior shoulder 8 make contact, thus assuring that the swab element is completely inside the outer tube 4 before withdrawing the device from the vagina. The outer tube 5 is closed with the cap 6, and placed in an environment where the temperature is greater than about 50° F., preferably about 72° F. (room temperature), and most preferably at about 98.6° F. (body temperature) in order to produce the most rapid results. If the woman has a yeast infection, brown colonies should grow throughout the media 3 after 12 hours and within about 16–18 hours, depending on the ambient temperature, these colonies cover the surface of the swab element.

This device can also be used reliably at any time except immediately after douching with a medicated douche.

In a further embodiment, the present invention also provides a test kit for diagnosis of vaginal yeast infections. The test kit comprises the first above described diagnosis device and a closable container for culturing vaginal secretion on the media of the device. The closable container can be a glass tube, for example.

The test kit can additionally comprise a series of diagnostic devices for diagnosing or suggesting the possible presence of, among others conditions and infections, other types of vaginal yeast infections. For example, components could be included for a suggestive test for *Trichomonas vaginalis* (trichomonas) and a diagnostic test for *Hemophilus vaginalis vaginitis* (HVV, Gardnerella, or vaginosis). The suggestive testing apparatus for trichomonas could comprise a strip of pH paper and a swab to transfer vaginal secretions to the pH paper; trichomonas is suggested when a change in the pH of the vagina is indicated by a color change of the pH paper as is well known in the art. The diagnostic apparatus for vaginosis could comprise a substrate that reacts with vaginal secretions to produce an odor and a swab for transferring the vaginal secretions to the substrate, this swab could be the same swab used to determine the pH. Diagnosis of vaginosis is made by sniffing to detect a fishy odor from the swab-contacted substrate as is well known in the art.

Of course, the skilled artisan can readily devise other combinations of diagnostic devices that include the device of the present invention.

EXAMPLES

The invention will now be illustrated by reference to non-limiting examples. Unless otherwise indicated, all percents, ratios, parts, etc. are by weight.

EXAMPLE 1

A home diagnosis device consisting of a paper support stick and a swab element about 1¼ inches long and about ¼ inch in diameter of white loosely woven USP Rayon attached to the support stick with sodium carboxymethyl cellulose was obtained from Hardwood Products of Guilford, Maine. The swab element was submerged in the reheated liquid culture media prepared as described below for about 1.5 seconds, until the media had infiltrated between the fibers of the swab element. The media was allowed to harden for about 60 seconds before the swab element was inserted into a transparent tube.

The swab element of the device was then inserted a sufficient distance into the vagina of a woman suspected of having a yeast infection. The device was removed and placed in a transparent tube that was capped. The tube was left at room temperature. That the woman had a yeast infection was confirmed in about 16 hours when the characteristic brown colonies covered the surface of the swab element.

Yeast infection was confirmed by traditional means using a cotton swab to swab the vagina and transfer inoculum to slants constructed using media identical to that described below, except the amount of agar used was only about 1.0%.

Preparation of Culture Media

The culture media was prepared by adding to one liter of water 30 g of agar, 5 g of bismuth ammonium citrate, 3 g of sodium sulfite, 10 g of dextrose, 10 g of glycine, and 1 g of yeast extract. The resulting mixture was heated until boiling and dispensed into sterile tubes. To impregnate the swabs, the tubes containing the media were heated to 72°–78° C. which liquified the media.

EXAMPLE 2

A home diagnosis device such as shown in FIG. 2 was constructed. The cap, outer tube, swab element, and inner holder utilized were sterilizable, semi-rigid, transparent plastic. The swab element was of white loosely woven USP Rayon, about 1¼ inches long and about ¼ inch in diameter manufactured by Hardwood Products of Guilford, Maine, and attached to the inner holder with sodium carboxymethyl cellulose. The swab element was prepared as described in EXAMPLE 1 by submerging it in the liquid culture media described in EXAMPLE 1 suitable for supporting the growth of yeast and allowing the media to solidify.

This device was inserted into the vagina about 1 inch or less (outer labia only) of a woman suspected of having a vaginitis infection. The swab element holder was pushed relative to the outer tube thereby exposing the media impregnated swab element to vaginal secretion inside the vagina that might contain yeast. The swab element, coated with vaginal secretion, was retracted into the outer tube, and the outer tube was withdrawn from the vagina. The outer tube was closed with the cap, and placed at room temperature to permit any yeast present to proliferate. That the woman had a yeast infection, was diagnosed in about 16 hours, when the characteristic brown colonies covered the surface of the swab element.

A yeast infection was confirmed by traditional means using a cotton swab to swab the vagina and transfer inoculum to slants constructed using media identical to that described in Table 1 for all ingredients except agar which constituted only 1.0% of the media of the slants. The use of 1.0% agar produced a softer medium that was otherwise identical to the media of the invention.

COMPARATIVE EXAMPLE 1

A device was constructed by immersing a tightly woven cotton swab, similar to that taught in U.S. Pat. No. 3,368,549, in liquid culture medium having the same composition and prepared in the same manner as described in EXAMPLE 1. The result was a globule of culture medium over the cotton swab. This device was compared to the above described embodiment of the invention by using both devices to test for a yeast infection by inserting each device about 2 inches into the vagina of a woman suspected of having a yeast infection, removing the devices, placing them in capped transparent tubes and placing the tubes at room temperature. After 12 hours, brown colonies began to grow rapidly on the swab element that embodied the invention. In contrast, there was no visible change on the prior art device. After 16 hours, the swab element of the invention was almost solidly covered with yeast colonies resulting in the characteristic marked color change. In contrast, there was still no visible change on the prior art device. In fact, it was only after 18 hours that some slight, barely discernible growth became visible on the surface of the prior art device.

To determine the reason for this surprising and unexpected difference between the embodiment of the invention and the prior art, the prior art device and the embodiment of the invention described in the paragraph above were cut open longitudinally, stained with gentian violet, and examined.

Figure 3:
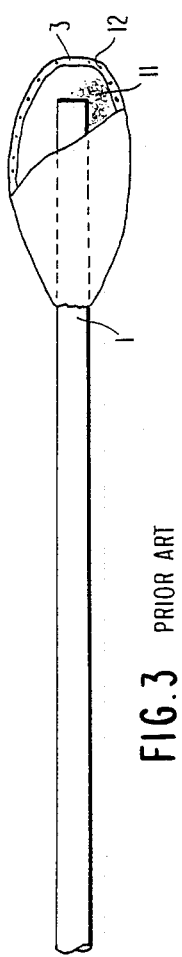
FIG. 3 is a partial cross-sectional view of a tightly woven swab of the prior art showing a layer of media on the swab fibers and yeast growing only on the surface of the media.

A pictorial representation of the prior art cotton swab, examined at a magnification of about 10× is shown in FIG. 3. The prior art cotton swab contained an extremely thin layer of media 3 on top of the densely packed cotton 11 on top of the support stick 1. An occasional yeast colony 12 was visible in the layer of media 3.

Figure 4:
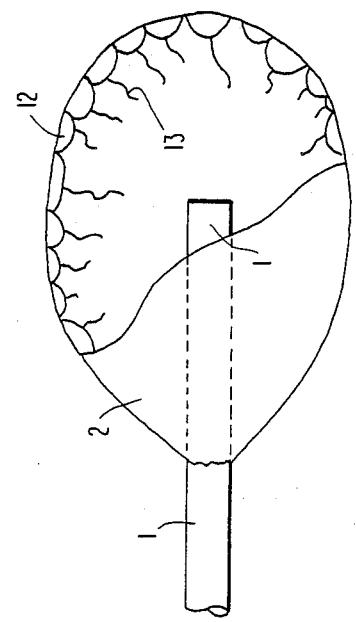
FIG. 4 is a partial cross-sectional view of an embodiment of one diagnosis device according to the claimed invention showing a swab element with penetration of the yeast colonies into the media.

The embodiment of the invention, also examined at a magnification of 10×, is shown at FIGS. 4 and 5. In contrast to the prior art cotton swab, the swab of the present invention as shown in FIG. 4 contained yeast colonies 12 growing in a thick layer on the surface of the swab element 2 and as finger-like projections 13 down into the rayon fibers. FIG. 5, shows that the surface layer of media 3 has abundant yeast colonies 12. The colonies 12 extend into media between the rayon fibers 14.

Figure 6:
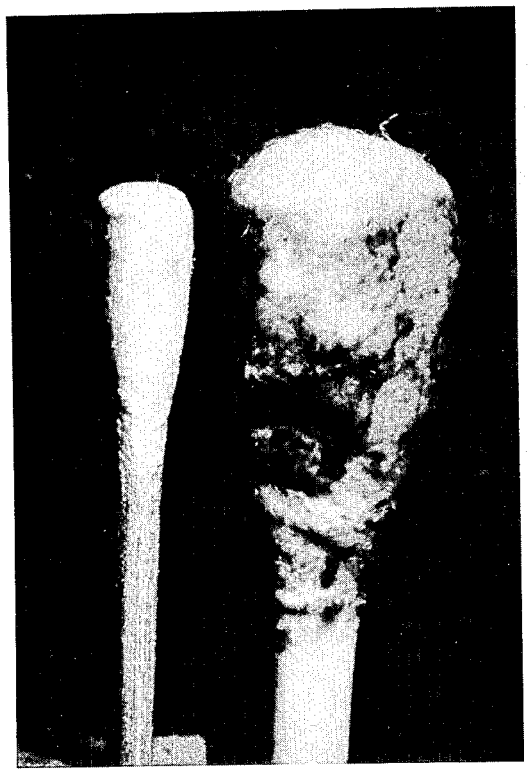
FIG. 6 is a photograph showing a prior art swab exhibiting little yeast growth (top) and a swab according to the invention showing extensive yeast colonies on its surface (bottom).

FIG. 6 is a photograph that shows the swab of COMPARATIVE EXAMPLE 1 and the cotton swab of the invention side by side. Each had been inserted into the vagina and then immediately withdrawn. The photograph was taken after culturing the vaginal secretion for 24 hours at 80° F. The photograph illustrates the dramatic difference between the visibility of the yeast colonies on the surface of the prior art swab and an embodiment of applicant's invention and shows how simple it is to confirm the presence of yeast with an embodiment of applicant's invention. In contrast, as the prior art device has no distinct colonies at all, confirmation is difficult.

While the invention has been described in detail and with reference to specific embodiments thereof, it will be apparent to one skilled in the art that various changes and modifications can be made therein without departing from the spirit and scope of the invention.

What is claimed is:

1. A diagnosis device for vaginal yeast infections comprising:
   a support stick;
   a swab having loosely woven fibers attached to one end of said support stick; and
   a growth media for culturing and diagnosing vaginal yeast infection infiltrated between said loosely woven fibers of said swab.

2. A diagnosis device for vaginal yeast infections according to claim 1, wherein said loosely woven fibers are composed of rayon.

3. A diagnosis device for vaginal yeast infections according to claim 2, wherein said swab has a pear shaped tip and is about 1⅛ inches long and about ½ inch in diameter.

4. A diagnosis device for vaginal yeast infections according to claim 2, wherein said growth media is an aqueous solution comprising:
   about 3.0 percent by weight agar,
   about 0.5 percent by weight bismuth ammonium citrate,
   about 0.3 percent by weight sodium sulfite,
   about 1.0 percent by weight dextrose,
   about 1.0 percent by weight glycine, and
   about 0.1 percent by weight yeast extract.

5. A home diagnosis device for vaginal yeast infections comprising:
   an outer tube;
   a cap, detachably connected to one end of said outer tube;
   a swab element having loosely woven fibers;
   a growth media for culturing and diagnosing vaginal yeast infection infiltrated between said loosely woven fibers of said swab element; and
   a holder for said swab element slideably mounted inside said outer tube.

6. A diagnosis device for vaginal yeast infections according to claim 5, wherein said loosely woven fibers are composed of rayon.

7. A diagnosis device for vaginal yeast infections according to claim 6, wherein said swab has a pear shaped tip and is about 1⅛ inches long and about ½ inch in diameter.

8. A diagnosis device for vaginal yeast infections according to claim 5, wherein said growth media is an aqueous solution comprising:
   about 3.0 percent by weight agar,
   about 0.5 percent by weight bismuth ammonium citrate,
   about 0.3 percent by weight sodium sulfite,
   about 1.0 percent by weight dextrose,
   about 1.0 percent by weight glycine, and
   about 0.1 percent by weight yeast extract.

9. A method for the diagnosis of vaginal yeast infections comprising the steps of:
   spreading the lips of the vulva;
   inserting into the vagina a swab of loosely woven fibers between which is infiltrated a growth media for culturing and diagnosing vaginal yeast infection;
   contacting vaginal secretion;
   removing said swab from the vagina;
   placing said swab in a sterile container;
   covering said container;
   culturing said vaginal secretion; and
   examining said swab for indications of vaginal yeast infection.

10. A method for the diagnosis of vaginal yeast infections according to claim 9, wherein said loosely woven fibers are composed of rayon.

11. A home diagnosis device for vaginal yeast infections according to claim 10, wherein said swab has a pear shaped tip and is about 1⅛ inches long and about ½ inch in diameter.

12. A method for the diagnosis of vaginal yeast infections according to claim 9, wherein said growth media is an aqueous solution comprising:
   about 3.0 percent by weight agar,
   about 0.5 percent by weight bismuth ammonium citrate,
   about 0.3 percent by weight sodium sulfite,
   about 1.0 percent by weight dextrose,
   about 1.0 percent by weight glycine, and
   about 0.1 percent by weight yeast extract.

13. A method for diagnosis of vaginal yeast infections comprising the steps of:
   inserting a tube into the vagina, said tube containing a swab element of loosely woven fibers between which is infiltrated a growth media for culturing and diagnosing vaginal yeast infection;
   sliding said swab element out of said tube and into contact with vaginal secretion;
   retracting said swab element into said tube and out of contact with said vaginal secretion;
   capping said tube;
   culturing said vaginal secretion in said tube containing said swab element; and
   examining said swab for indications of vaginal yeast infection.

14. A method for the home diagnosis of vaginal yeast infections according to claim 13, wherein said loosely woven fibers are composed of rayon.

15. A home diagnosis device for vaginal yeast infections according to claim 13, wherein said swab has a pear shaped tip and is about 1⅛ inches long and about ½ inch in diameter.

16. A method for the home diagnosis of vaginal yeast infections according to claim 13, wherein said growth media is an aqueous solution comprising:
   about 3.0 percent by weight agar,
   about 0.5 percent by weight bismuth ammonium citrate,
   about 0.3 percent by weight sodium sulfite,
   about 1.0 percent by weight dextrose,
   about 1.0 percent by weight glycine, and
   about 0.1 percent by weight yeast extract.

17. A test kit for diagnosis of vaginal yeast infections comprising:
   (a) a diagnosis device for vaginal yeast infections comprising a support stick, a swab having loosely woven fibers attached to one end of said support stick, and a growth media for culturing and diagnosing vaginal yeast infection infiltrated between said loosely woven fibers of said swab; and (b) a closable container receiving said support stick and swab for culturing vaginal secretion on said growth media of said device.

18. A test kit for diagnosis of vaginal yeast infections according to claim 17 wherein said loosely woven fibers are composed of rayon.

19. A test kit for diagnosis of vaginal yeast infections according to claim 18 wherein said swab has a pear shaped tip and is about 1¼ inches long and about ½ inch in diameter.

20. A test kit for diagnosis of vaginal yeast infections according to claim 18 wherein said growth media is an aqueous solution comprising:
   about 3.0 percent by weight agar,
   about 0.5 percent by weight bismuth ammonium citrate,
   about 0.3 percent by weight sodium sulfite,
   about 1.0 percent by weight dextrose,
   about 1.0 percent by weight glycine, and
   about 0.1 percent by weight yeast extract.

* * * * *